United States Patent [19]

Speck et al.

[11] Patent Number: 5,010,061
[45] Date of Patent: Apr. 23, 1991

[54] GUAR FLOUR

[76] Inventors: Ulrich Speck, Benediktinerstrasse 50, D-1000 Berlin 28; Panayiotis Roumeliotis, Frankfuter Strasse 12, D-6100 Darmstadt, both of Fed. Rep. of Germany

[21] Appl. No.: 564,673

[22] Filed: Aug. 6, 1990

Related U.S. Application Data

[63] Continuation of Ser. No. 362,489, Jun. 7, 1989, abandoned, which is a continuation of Ser. No. 31,999, Mar. 27, 1987, abandoned.

[30] Foreign Application Priority Data

Apr. 18, 1986 [DE] Fed. Rep. of Germany ....... 3613219

[51] Int. Cl.$^5$ ...................... A61K 31/715; C08B 37/00
[52] U.S. Cl. ...................... 514/54; 514/909; 514/962; 536/52; 536/114; 424/500
[58] Field of Search ............ 514/54, 909, 962; 424/500; 536/52, 114

[56] References Cited

U.S. PATENT DOCUMENTS

| | | | |
|---|---|---|---|
| 2,662,882 | 12/1953 | Christianson et al. | 536/114 |
| 3,313,800 | 4/1967 | Jackson, Jr. et al. | 536/114 |
| 3,700,612 | 10/1972 | Fath et al. | 536/114 |
| 4,269,975 | 5/1981 | Rutenberg et al. | 536/114 |
| 4,520,017 | 5/1985 | Tunc | 514/54 |
| 4,576,932 | 3/1986 | Sorbini | 514/54 |
| 4,675,312 | 6/1987 | Nittner et al. | 514/54 |
| 4,798,888 | 1/1989 | Symes et al. | 536/123 |

FOREIGN PATENT DOCUMENTS

| | | | |
|---|---|---|---|
| 0007619 | 2/1980 | European Pat. Off. | 514/54 |
| 0080673 | 6/1983 | European Pat. Off. | 514/54 |
| 3139920 | 4/1983 | Fed. Rep. of Germany | 514/54 |
| 2021948 | 12/1979 | United Kingdom | 514/54 |
| 2030583 | 4/1980 | United Kingdom | 514/54 |

OTHER PUBLICATIONS

International Dictionary of Medicine and Biology, vol. 11, John Wiley & Sons, N.Y.: 1986, p. 1109.

*Primary Examiner*—Ronald W. Griffin
*Assistant Examiner*—Nancy S. Carson
*Attorney, Agent, or Firm*—Millen, White & Zelano

[57] ABSTRACT

The instant invention relates to guar flour formulations, to be ingested, wherein the formulations contain natural guar flour having a particle size diameter or 50 μm to 1500 μm and neither containing nor having been treated with any additive which substantially affects its form or consistency or which substantially delays or reduces the swelling ability of the flour.

26 Claims, No Drawings

GUAR FLOUR

This application is a continuation of application Ser. No. 07/362,489, filed June 7, 1989, which is a continuation of application Ser. No. 07/031,999, filed Mar. 27, 1987, both abandoned.

Swelling agents are usually natural or semi-synthetic indigestible polysaccharides being able to form viscous jellies. They keep the contents of the gut soft and retain water. In addition, the peristalsis is increased by the contents of the gut. Some examples of swelling agents or gums are methylcellulose, carboxymethylcellulose, agar-agar and guar flour.

In connection with all swelling agents care must be taken that sufficient water is drunk since otherwise the contents of the intestine stick together and may cause an ileus. Guar flour has the ability of quickly swelling up in water. Already small quantities of guar flour in water result in large volumes of jelly. Guar flour is a natural product, i.e. a polysaccharide consisting of about two parts of mannose and one part of galactose. After oral application guar flour is not enzymatically hydrolysed and therefore it is not absorbed. It is known as being well tolerated.

In medicine, guar gum has come into use for several reasons:

(a) It delays the absorption of nutrients, particularly of glucose when taken before the meals, as was shown in Lembcke. B.; Ebert, R.; Ptok, M.; Caspary, W.F.; Crentzfeldt, W.; Schicha, H.; Emrich, D.; Role of gastrointestinal transit in the delay of absorption by viscous fibre (guar); Hepato-gastro enterol. 31,4; 183–186 (1984).

(b) Moreover, it lowers the cholesterin content of the blood, as was shown in Bosello, O.; Caminacini, L.; Zocca, I.; Garbin, U.; Ferrari, F.; Davoli, A.; Effects of guar gum on plasma lipoproteins and apoliproteins C-II and C-III in patients affected by familial combined hyperlipoproteinemia; The American Journ. of Clinical Nutrition 40,6; 1165–1174 (1984).

(c) It has appetite reducing effects.

(d) It regulates the peristalsis of the intestine.

Guar is particularly used under the aspects of (a) and (b) also as a supplement to a diet and an additive to foodstuffs.

One problem in connection with the use of guar gum as a drug or an additive to foodstuffs is the necessary high dosage. For the retardation of the glucose absorption as well as for the lowering of the cholesterin level, usually a daily dose of at least 10 g guar is necessary.

Usually, guar is made available as a white to yellowish flour being largely neutral with respect to its taste. That flour cannot be taken in its dry state, since it would paste mouth, throat and gullet. Mixed in only some water, the flour results in a stiff jelly which can also not be swallowed. Moreover, the commercial guar flours tend to form large lumps if they are not stirred very intensely. Only when mixed in a great quantity of water, a solution of sufficiently low viscosity is obtained which can be drunk.

In case of commercial guar flour there even exists a high risk of suffocation because the swelling process starts immediately after the oral ingestion of the dry material. The alternative extreme would be the dispersion and dilution of the guar flour to obtain a drinkable solution. This is also out of question since guar swells within seconds to such an extent that for instance at least 400 ml water would be necessary for preparing only 4 g guar flour. That problem has been solved until now by adding excipients (gelatine, starch, buffers, silica gel). These excipients improved the pharmaceutical quality of the products as far as the oral ingestion is concerned, however, entailed several problems:

(a) The dose of guar being high, anyhow, is even increased by the therapeutically ineffective and partly even undesired additives.

(b) The excipients get into interaction with the guar flour and can reduce the desired swelling ability of the guar in the gut. A complete swelling of the guar is, however, a prerequisite for the desired pharmacological effect.

(c) On principle, the preparations get a particle character, i.e. macroscopic guar particles having a diameter of 1 mm to >1 cm are administered. These particles must either be taken orally after having been suspended in water or in the form of tablets.

Due to the high dose, the repeated daily application of several large guar tablets or of great quantities of dry granules with water can hardly be acceptable to elderly people. In case of all particle-containing media, in addition to this, partly swollen portions stick to the mouth thereby causing problems particularly for people with artificial denture. A further disadvantage of particle-containing suspensions lies in the fact that the guar particles either swim at the surface or rapidly sediment so that the patient has less than one minute for drinking a fairly homogeneous suspension after quick stirring. That results in a refusal of the drug or at least in its irregular use. The unsatisfactory compliance is the most serious problem in the guar therapy.

Thus it is an object of the present invention to give the guar flour a form which enables even elderly and sensitive people to repeatedly take daily quantities of about 3 g to 5 g. In that case neither big tablets or capsules nor such preparations of drugs which are difficult to be swallowed, as for instance large quantities of granules, should be chosen, nor should the guar flour have to be drunk in too large quantities of liquids, form lumps or have unpleasant characteristics as to taste, or be inconvenient for the patient because of its consistency. On the other hand, the advantageous characteristics of the guar flour described above shall be maintained.

According to the present invention that problem is solved by the fact that 90 to 100 percent of weight of the guar flour have a particle size with a diameter of 50 $\mu$m to 1,500 $\mu$m.

This constitutes a surprisingly simple solution of the problem having been worked at for years. As a result, a pure guar flour is produced without using additive substances, which guar flour can easily be taken with little water, without any risks and in a comfortable way.

Since no special additives for reducing or delaying the swelling ability of guar are required, there also does not exist any risk that the guar might not swell completely after having been ingested.

The basis of the present invention is the observation that the fine share (particles <<100 $\mu$m) of the usual guar flour even though its quantity is very small, is responsible for the extremely rapid gelation of the aqueous suspension of the usual guar flours. Thus, for instance 4 g of usual guar flour—put into 150 to 200 ml water—become undrinkably viscous within 10 to 30 seconds. A further essential disadvantage of the usual guar flour is the almost unavoidable formation of lumps of non-swollen flour included in an impermeable layer of jelly. These lumps make the swallowing of the anyway highly viscous solutions even more difficult. If one sieves the portion of fine particles so that for instance >95% of the remaining guar flour consist of particles having a size of 100 μm to 500 μm, one obtains, after stirring 4 g flour into 100 to 200 ml water, a homogeneous sufficiently fluid suspension. The correspondingly chosen flour is excellently wettable, sinks down into the liquid at once, is easy to stir, does not form any lumps and does not comprise any particles noticeable in the mouth. At room temperature, it remains sufficiently fluid for at least five minutes to be drunk. When stirred in water, the described flour is largely neutral as to taste, and in fruit-juice or other fluids or foodstuffs it takes their genuine taste.

An agent produced according to the present invention is for instance chemically unchanged guar flour without any additives, characterized by a share of >90%, preferably ≧98% guar particles having a particle diameter of 50 μm to 1,500 μm, preferably 100 to 500 μm. The dosage can for instance take place by means of a measuring spoon from a storage bin or, more exactly and hygienically more acceptable by packing the individual dose in separate containers. The individual dose is 3 to 6 g, preferably 4 g genuine guar flour. Two to five individual doses are taken per day. The flour is mixed with a corresponding volume of aqueous liquid, preferably 100 to 200 ml/per 4 g flour, and drunk within about 0 to 20, preferably 0 to 5 minutes after complete mixing.

Flavourings and aromas, foaming agents such as $NaHCO_3$, as well as citric acid, vitamines, minerals and particularly drugs the absorption of which shall be delayed, can be added to the flour. The latter variant is of special importance when the diseases of the patient require a simultaneous treatment with guar and a drug which usually reaches either too high blood levels (for instance oral anti-diabetics) or shows a too short half-life (for instance lipid lowering agents).

Moreover, the guar flour according to the invention can he administered orally for lowering the blood cholesterin level or for regulating the peristalsis.

During diagnostic examinations of the stomach or the intestine, a uniform filling of the lumen or a wall covering may be desired. Also in that case, the use of the described guar preparation is advantageous particularly because of its good dispersibility and the pleasant taste. Without any problems the guar preparations as described above can be mixed with all kinds of contrast media.

In the stomach and in the intestine the desired high viscosities are achieved by complete swelling even of the larger guar particles. In case of osmotically active contrast agents the addition of sufficient quantities of guar can evidently reduce the diarrhoe caused by the same.

The addition of the substances mentioned, particularly also of the taste determining substances, can very well take place by the choice of the liquid (for instance fruit-juices) or other materials in which the guar flour is suspended. Thereby, the choice of the taste is left to the patient.

The invention refers to all kinds of preparations of drugs and contrast agents showing contents of the guar flour according to the invention.

Aqueous suspensions are preferred in which the contents of the guar flour amounts to at least 2% of weight.

The particle fractions necessary according to the invention are obtained by usual separation proceedings, for instance by sieving, from guar flour being on the market.

EXAMPLE 1

4 g guar flour, particle size ≧98% <100 μm >500 μm packed in bags. The contents of the bag is suspended in 150 ml water at room temperature, and drunk soon after.

EXAMPLE 2

About 6 g guar flour, particle size 95% of weight >200 μm <1,000 μm, are taken from a storage bin with a measuring spoon and suspended in 200 ml gas-free orange fruit-juice and drunk within 5 minutes.

EXAMPLE 3

4 g guar flour, particle size 90% of weight <50 μm >500 μm, are separately packed in aluminum foil. The entire contents of one individual packing is added to 150 ml cold (ca. 10° C.) water and drunk rapidly.

EXAMPLE 4

4 g guar flour, particle size 98% of weight >100 μm <1,500 μm, are suspended in 150 ml freshly pressed cold fuit-juice (orange, apple) and drunk soon after.

EXAMPLE 5

3 g guar flour, particle size ≧98% of weight >100 μm <500 μm, are uniformly mixed with 50 mg vitamin C, 20 mg $MgCO_3$ and 20 mg $NaHCO_3$ and packed in a bag. The entire contents of a bag is stirred into 100 ml cold water and drunk soon after.

EXAMPLE 6

4 g guar flour, particle size ≧98% of weight >100 μm <500 μm, are uniformly mixed with 3.5 mg glibenclamid as anti-diabetically active agent, and filled into a bag. The entire contents of a bag is suspended in 150 ml water and drunk soon after.

EXAMPLE 7

4 g guar flour, particle size ≧98% of weight <100 μm >500 μm, are uniformly mixed with 50 mq magnesiumpyridoxalphosphateglutaminat (I) and 50 mg $MgCO_3$ (II) whereby the 1% (I) and the 0.1% (II) solution resp. of I and II is drawn up the guar flour in 80% ethanol, and the alchol is removed at 40° C. under careful stirring. The residue is dried at reduced pressure to a content of water of ≦5%. The entire preparation is packed into aluminum bags. The content of the bags has to be stirred into 150 ml water and to be drunk within about 5 minutes.

EXAMPLE 8

8 g guar flour, particle size 95% of weight >50 μm <250 μm, are mixed with a quantity of sodium-meglumine diatrizoate (10:66) containing 10 g iodine, and packed into aluminum coated bags. Immediately before use, the contents of the bag is stirred into 1 l of water and drunk slowly. The examination takes place with the computerized tomography shortly or 16 hours maximum after intake of the preparation. Optionally. 500 ml to 1,000 ml can again be taken shortly before the examination.

COMPARATIVE TESTS

Included in the test were the preparations GLUCOTARD® (guar flour pressed to tablets under addition of silica gel) of Boehringer Mannheim, and GUAREM® (guar granules with additive of excipients) of Lääketehdas Remeda, Finland, approved as drugs, the usual guar floursMüggenburg, DIAGUAR-63 and DIAGUAR-250 as well as a preparation (GU-052) according to Example 1 of the present invention.

Evaluation criteria were "suitability for oral application" as well as "complete swelling". The criteria aimed at for making the preparations more acceptable to the patients were
- no increase of the dose due to additives
- no tablets or particles (which due to the high dose have to be either large in size or large in number)
- in case of suspensions a uniform distribution in water without any residence time at the surface or rapid sedimentation or even clotting of the material
- a neutral taste
- drinkability, objectivated under the conditions defined in Table 1 as flowability.

The swelling capacity (as a criterion of efficacy) was valued by means of the viscosity of a 1% preparation in water after limited swelling time.

Method of determining the drinkability

The guar flour is first stirred in the respective volume of water at 18° C. Then, after about 30 seconds, the homogeneous suspension is introduced into a cylindrical storage bin with a capacity of 110 ml and a diameter of about 15 mm and with an added cylindrical draining tube of 20 mm length and an opening of 5 mm in diameter at the bottom. The outlet opening is set free exactly 1 minute after the guar material has come into contact with the water. Subsequently, the time for the outflow of 10 and 30 ml is measured. In a second test, the outlet opening is set free only after a swelling time of five minutes.

Assessment

As long as the guar suspension flows out of the container it is regarded as drinkable.

TABLE 1

Criteria for the evaluation of guar preparations to be taken orally and comparative test of different preparations

| | Example 1 GU-052 | GLUCOTARD® | GUAREM® | GUAR Muggenburg | DIAGUAR 063 | DIAGUAR −250 |
|---|---|---|---|---|---|---|
| quantity (g) | 4.0 | 5.0 | 4.75 | 4.0 | 4.0 | 4.0 |
| excipients therein (g) | — | 1.133 | 0.25 | — | — | — |
| tablets suspensions | — | yes | — | — | — | — |
| material swims | — | — | — | yes | yes | — |
| material sediments | very slowly | very quickly | very quickly | — | — | — |
| forms clots | — | — | — | yes | badly | very little |
| uncomfortable particles in the mouth | — | yes | very disturbing | yes clots | yes clots | — |
| taste | neutral | somewhat sour | neutral | neutral | neutral | neutral |
| flowability | | | | | | |
| after 1 min 18° C. (30 ml in sec) | 3.4 | * | 2.7 | 12 | 17 | 26 |
| after 5 min 18° C. (10 ml in sec) | 106 | * | <1.0 | not flowable | not flowable | not flowable |
| swelling capability viscosity 1% after 2 h, 20° C. (cP) | 5,350 | 650 | 1,360 | * | 5,500 | 5020 |

"—" means "zero" or "no"
"*" means "no measuring"

Result

The preparation GU-052 according to the present invention corresponds best to the criteria aimed at. It does not comprise any additives and no perceivable particles, can easily and homogeneously be suspended in water, forms no lumps, does not rise to the surface nor sediments, is neutral as to taste and, when suspended in 200 ml (=one cup of) water remains to be easily drinkage for at least 5 minutes. The preparation GU-U052 according to the present invention, contrary to the preparations GLUCOTARD® and GUAREM®, remains fully swellable and thus meets an essential requirement for a good effectiveness. This refers particularly to the application possibilities in case of which a retardation of an undesiredly rapid absorption is concerned (for instance glucose for diabetics).

We claim:

1. In a method of administering guar flour to a human desiring such administration comprising directly adding said guar flour to an aqueous medium and directly thereafter orally administering said guar flour, the improvement wherein said guar flour added to said aqueous medium to be orally administered is natural guar flour having a particle size distribution wherein 90 to 100% by weight of the guar flour particles have a diameter of 50 μm to 1500 μm and said natural guar flour having said distribution neither contains nor has been treated with additives which substantially affect the form or consistency of said guar flour particles or which substantially delay or reduce the swelling ability of said guar flour particles.

2. A method of claim 1, wherein at least 98% by weight of said guar flour particles have a diameter of 50 μm to 1000 μm.

3. A method of claim 20, wherein at least 95% by weight of said guar flour particles have a diameter of 100 μm to 500 μm.

4. A method of claim 1 for oral administration of guar flour for retardation of the resorption of a nutrient or a drug.

5. A method of claim 4 for oral administration of guar flour for lowering the cholesteric level of the blood.

6. A method of claim 4 for oral administration of guar flour for regulation of intestinal peristalsis.

7. A method of claim 4 for oral administration of guar flour for retarding glucose absorption.

8. A method of claim 4 for oral administration of guar flour for retarding glucose absorption and lowering the cholesteric level.

9. A method of claim 1, wherein said guar flour is coadministered with an oral diagnostic contrast agent.

10. A method of claim 1 for oral administration of guar flour, wherein said guar flour is coadministered with an oral diagnostic contrast agent.

11. A method of claim 1, wherein said natural guar flour contains a flavoring or aromatic substance, a drug, or a diagnostic agent.

12. A method of preparing an individual packing of guar flour for administration to a human directly after adding said guar flour to an aqueous medium, consisting essentially of directly placing into said packing natural guar flour having a particles size distribution wherein 90 to 100% by weight of the guar flour particles have a diameter of 50 μm to 1500 μm, said natural guar flour having said distribution neither containing nor having been treated with additives which substantially affect the form or consistency of said guar flour particles or which substantially delay or reduce the swelling ability of said guar flour particles.

13. A method of claim 12, wherein at least 98% by weight of said guar flour particles have a diameter of 50 μm to 1000 μm.

14. A method of claim 13, wherein at least 95% by weight of said guar flour particles have a diameter of 100 μm to 500 μm.

15. An individual packing of guar flour prepared by the method of claim 12.

16. A method of claim 12, wherein said natural guar flour contains a flavoring or aromatic substance, a drug, or a diagnostic agent.

17. A individual packing of guar flour for administration to a human directly after adding said guar flour to an aqueous medium, consisting essentially of an individual packing having placed therein natural guar flour having a particle size distribution wherein 90 ti 100% by weight of the guar flour particles have a diameter of 50 μm to 1500 μm, said natural guar flour having said distribution neither containing nor having been treated with additives which substantially affect the form or consistency of said guar flour particles or which substantially delay or reduce the swelling ability of said guar flour particles.

18. An individual packing of guar flour of claim 17, wherein at least 98% by weight of said guar flour particles have a diameter of 50 μm to 1000 μm.

19. An individual packing of guar flour of claim 17, wherein at least 95% by weight of said guar flour particles have a diameter of 100 μm to 500 μm.

20. An individual packing of guar flour of claim 17, wherein said natural guar flour contains a flavoring or aromatic substance, a drug, or a diagnostic agent.

21. A guar flour formulation suitable for oral administration to a human consisting essentially of (a) a flavoring or aromatic substance, a drug, or a diagnostic agent and (b) natural guar flour having a particle size distribution wherein 90 to 100% by weight of the guar flour particles have a diameter of 50 μm to 1500 μm, said natural guar flour having said distribution neither containing nor having been treated with additives which substantially affect the form or consistency of said guar flour particles or which substantially delay or reduce the swelling ability of said guar flour particles.

22. A guar flour formulation of claim 21, wherein at least 98% by weight of said guar flour particles have a diameter of 50 μm to 1000 μm.

23. A guar flour formulation of claim 22, wherein at least 95% by weight of said guar flour particles have a diameter of 100 μm to 500 μm.

24. An aqueous medium for coadministration of a guar flour and a flavoring or aromatic substance, a drug, or a diagnostic agent, comprising a mixture of an aqueous medium and a guar flour formulation of claim 21.

25. An aqueous medium of claim 21 further comprising an oral diagnostic contrast agent.

26. A guar flour formulation of claim 21, wherein said natural guar flour contains a flavoring or aromatic substance, a drug, or a diagnostic agent.

* * * * *